(12) United States Patent
Berkovitch et al.

(10) Patent No.: US 7,927,345 B2
(45) Date of Patent: Apr. 19, 2011

(54) LANCET CARTRIDGES AND LANCING DEVICES

(75) Inventors: Frederick Berkovitch, Cambridge, MA (US); Brad Boozer, Marblehead, MA (US); Joseph Flaherty, Westford, MA (US); Timothy Golnik, Boxford, MA (US); Sridhar Iyengar, Salem, NH (US); Malia Kilpinen, Cambridge (GB); Sonny Vu, Salem, NH (US)

(73) Assignee: AgaMatrix, Inc., Salem, NH (US)

( * ) Notice: Subject to any disclaimer, the term of this patent is extended or adjusted under 35 U.S.C. 154(b) by 891 days.

(21) Appl. No.: 11/555,974

(22) Filed: Nov. 2, 2006

(65) Prior Publication Data
US 2008/0109024 A1 May 8, 2008

(51) Int. Cl.
*A61B 5/151* (2006.01)
(52) U.S. Cl. ...................................................... 606/181
(58) Field of Classification Search .................. 600/583, 600/564, 566, 567; 606/181–182
See application file for complete search history.

(56) References Cited

U.S. PATENT DOCUMENTS

| | | | | |
|---|---|---|---|---|
| 3,138,161 | A * | 6/1964 | Allen | 604/99.01 |
| 5,514,152 | A | 5/1996 | Smith | |
| 5,741,288 | A | 4/1998 | Rife | |
| 6,036,924 | A * | 3/2000 | Simons et al. | 422/100 |
| 6,071,294 | A | 6/2000 | Simons et al. | |
| 6,358,265 | B1 | 3/2002 | Thorne, Jr. et al. | |
| 6,472,220 | B1 | 10/2002 | Simons et al. | |
| 6,540,762 | B1 | 4/2003 | Bertling | |
| 6,540,763 | B2 * | 4/2003 | Teo et al. | 606/182 |
| 6,616,616 | B2 | 9/2003 | Fritz et al. | |
| 6,651,989 | B2 | 11/2003 | Johnson | |
| 2002/0087180 | A1 * | 7/2002 | Searle et al. | 606/181 |
| 2003/0153939 | A1 | 8/2003 | Fritz et al. | |
| 2003/0187470 | A1 | 10/2003 | Chelak et al. | |
| 2003/0212424 | A1 | 11/2003 | Briggs et al. | |
| 2004/0230216 | A1 * | 11/2004 | Levaughn et al. | 606/181 |
| 2005/0085840 | A1 | 4/2005 | Yi et al. | |

* cited by examiner

*Primary Examiner* — Todd E Manahan
*Assistant Examiner* — Ashley Cronin
(74) *Attorney, Agent, or Firm* — Larson & Anderson, LLC

(57) ABSTRACT

A lancet cartridge has a U-shaped support with a pair of anchor portions, a base portion, and a pair of deformable leg portions connecting the anchor portions to the base portion. The pair of deformable leg portions change shape from an initial shape to an extended shape in response to an external applied force and recover to a retracted shape upon removal of the force. The lancet cartridge also has a lancet having a tip end, an opposing base end, and an axis extending between the tip end and the base end. A portion of the lancet is disposed between the pair of deformable leg portions of the U-shaped support. The lancet is movable between a starting position, an extended puncturing position, and an ending position along the axis of the lancet in a path defined by the U-shaped support. When the lancet is in the starting position, the tip end of the lancet is disposed at least partially through the base portion of the U-shaped support, and the U-shaped support is in the initial shape. When the lancet is in the extended puncturing position, the tip end of the lancet is extended through the base of the U-shaped support, and the U-shaped support is in the extended shape. When the U-shaped support recovers to its retracted shape upon removal of the force, the lancet is retracted to the end position.

20 Claims, 17 Drawing Sheets

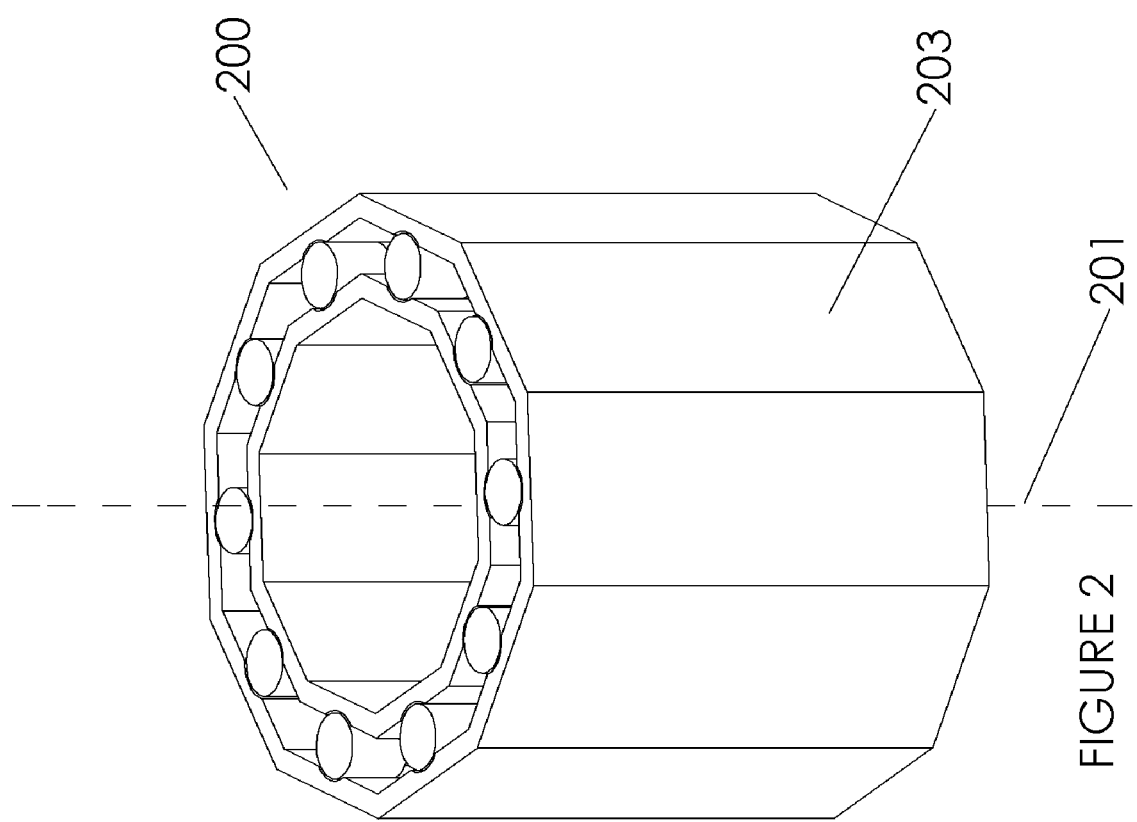

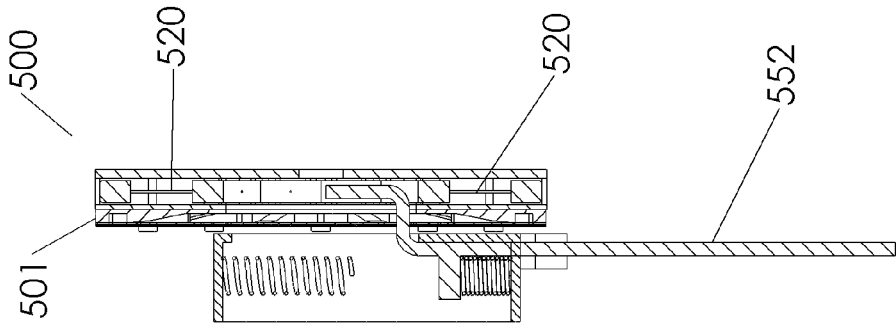
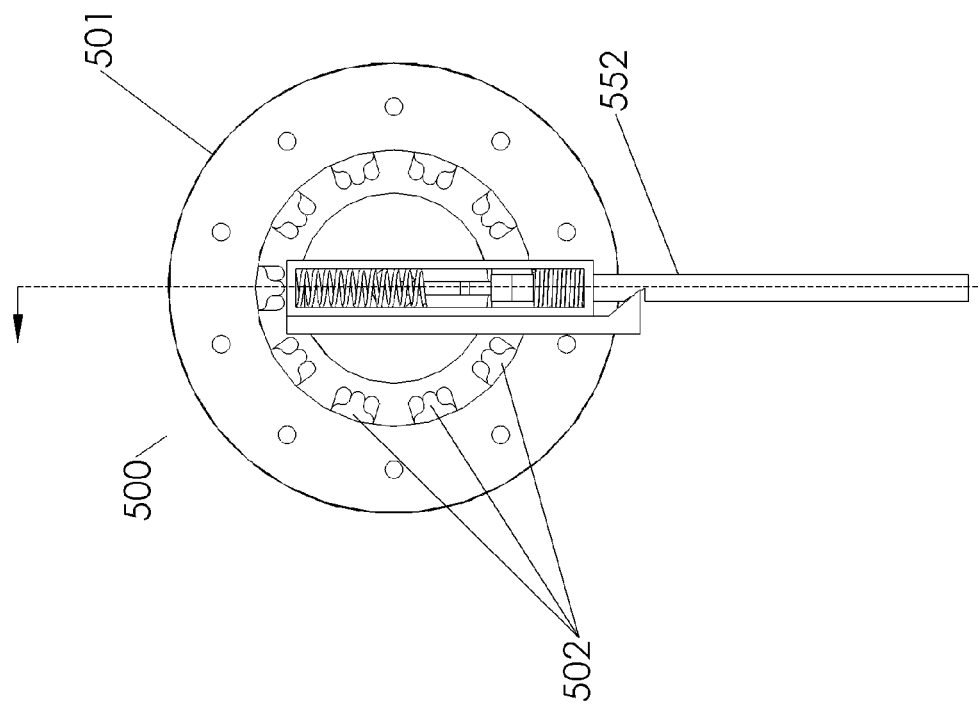

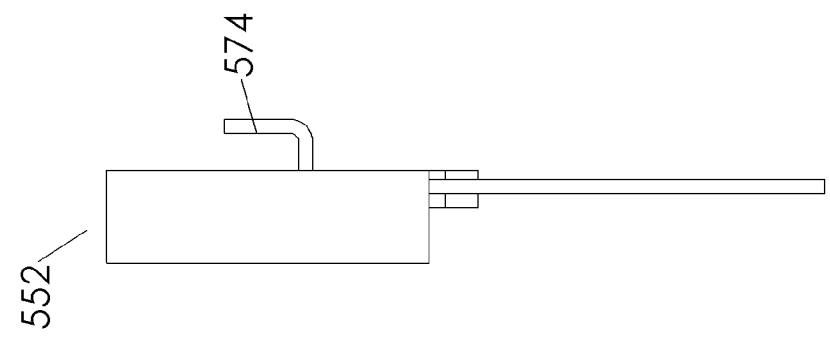
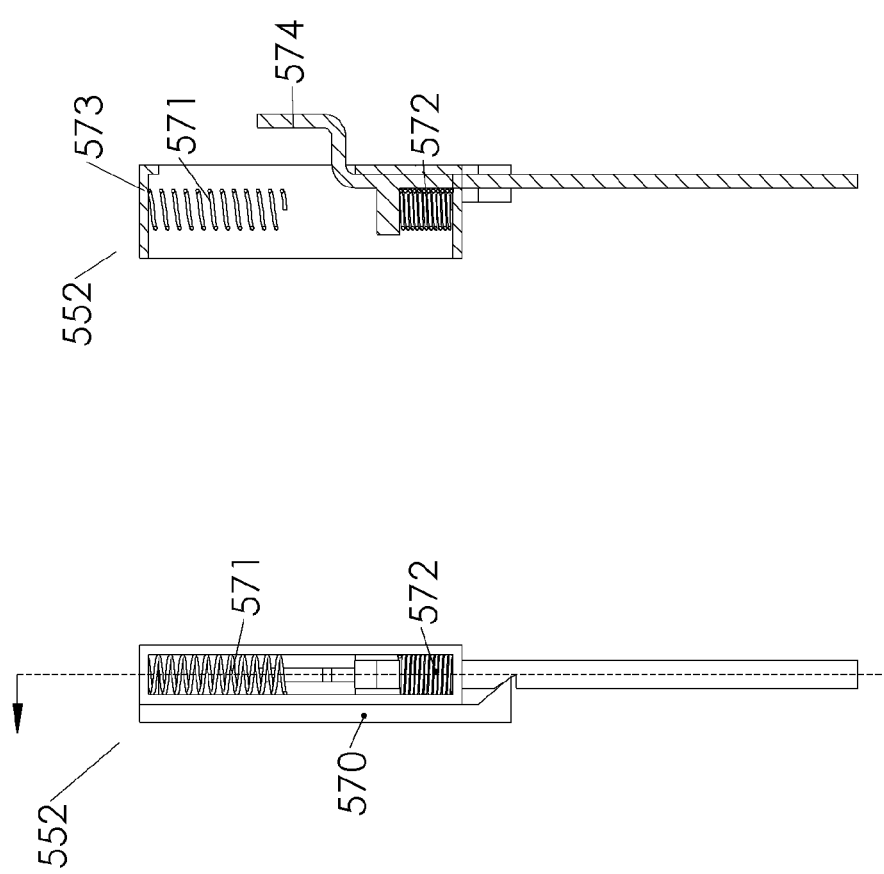
FIGURE 5E  FIGURE 5D  FIGURE 5C

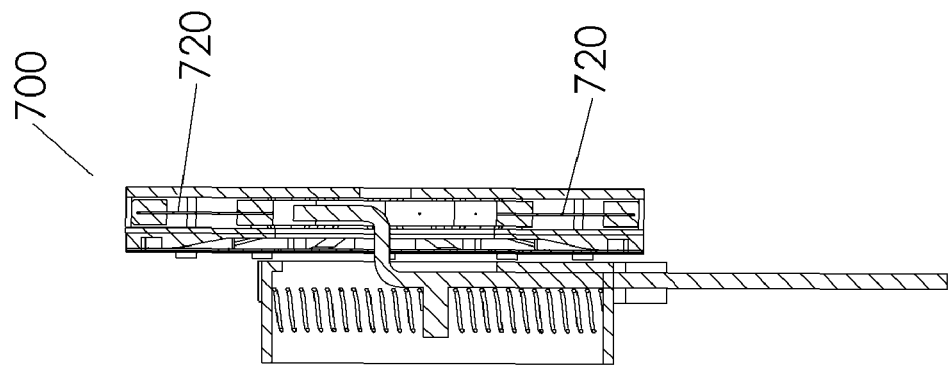
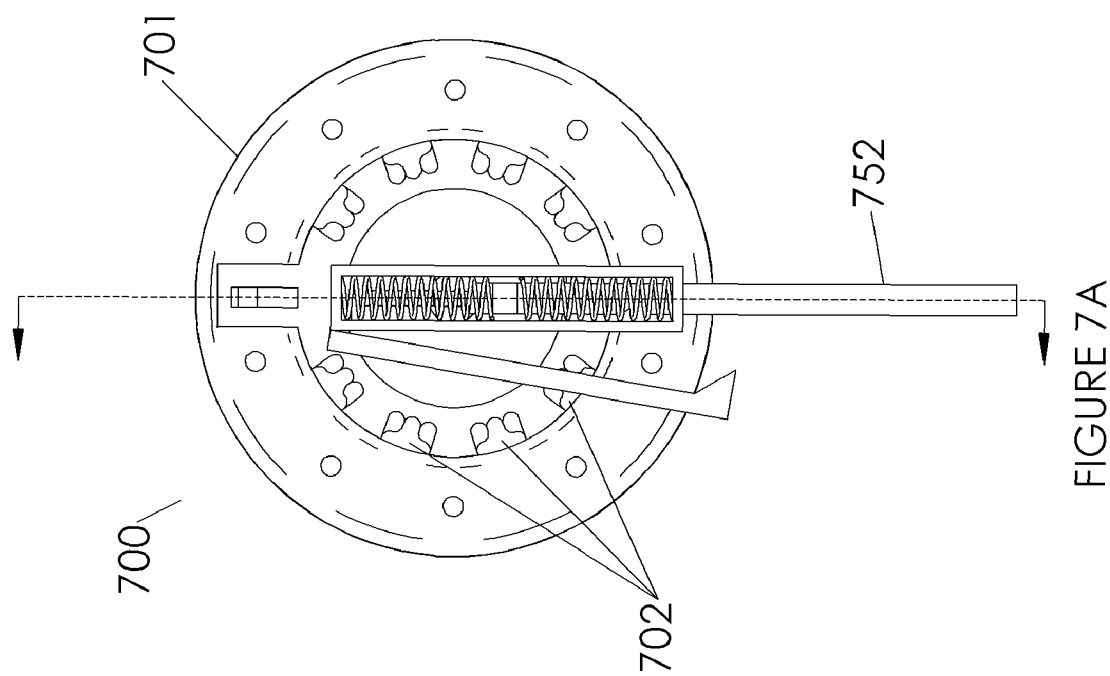
FIGURE 7B
FIGURE 7A

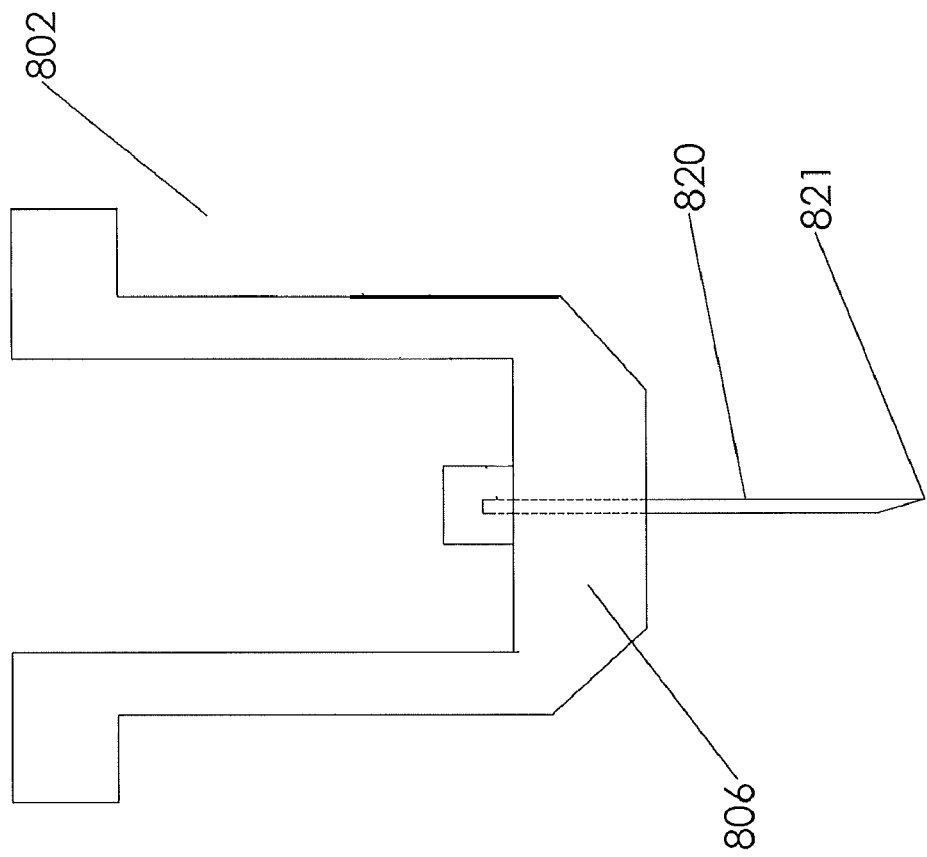

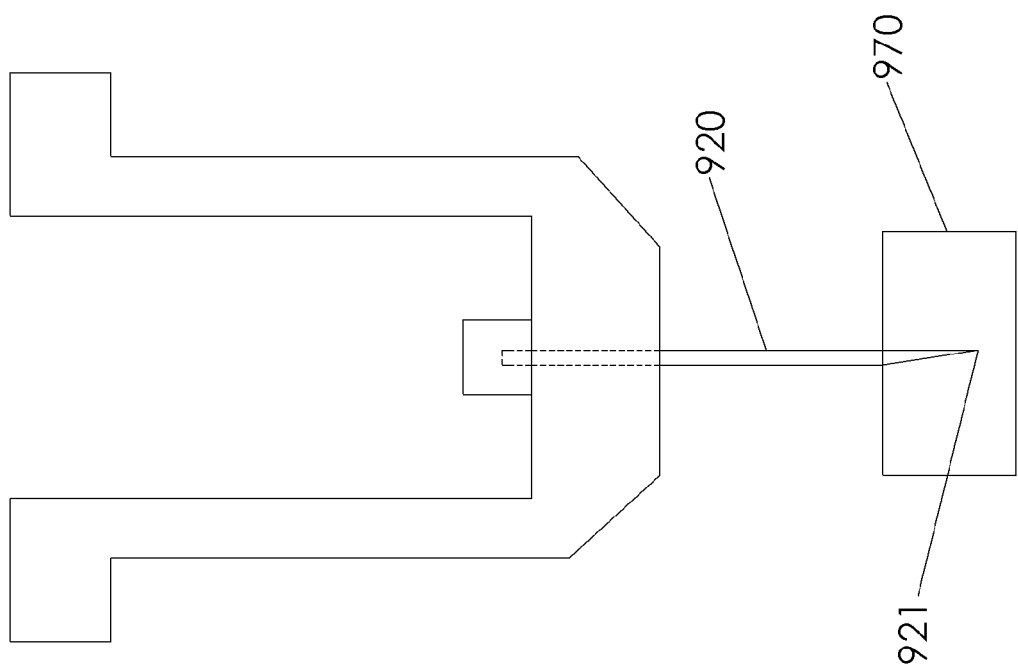

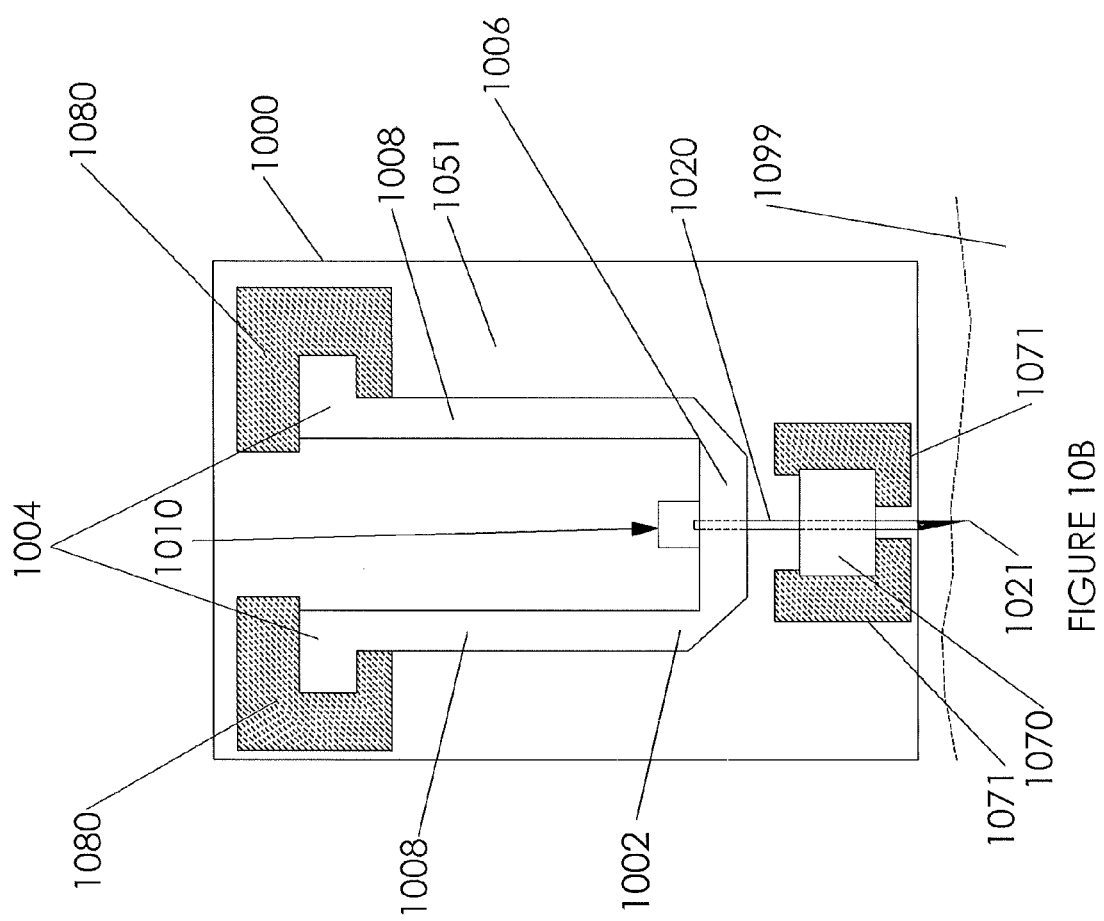

LANCET CARTRIDGES AND LANCING DEVICES

BACKGROUND OF THE INVENTION

This application relates to a lancet cartridge suitable for use with a lancing device by a diabetic, or other user, to obtain small samples of blood, interstitial fluid, or tissue from the fingers, forearm, or other body portions. The invention also relates to an improved lancing device comprising the lancet cartridges of the present invention.

Lancing devices are well known. Most include an outer casing, a lancet (e.g. a needle or a blade), a priming mechanism to produce and store potential energy (usually in a coil spring), and a trigger to release the stored energy to produce a lancing motion of the lancet with a hammer. Some also include a cap to cover the lancet needle in order to preserve sterility prior to use as well as helping avoid unintended skin piercing with the lancet prior to and after use. More complex lancing devices may even contain motor driven lancets that are extended and retracted by a computer driven process. Lancing devices may be designed to receive a lancet cartridge which preferably is a disposable part that includes one or more lancets. These lancet cartridges typically have the lancets disposed in a base or housing that is adapted to fit within and be removable from a lancing device that allows a hammer to strike and move the lancet in a lancing motion Lancing devices have many uses, but the most common use is by diabetic patients to draw blood and to monitor their blood sugar levels. It would not be unusual for a diabetic patient to need to use such a device several times a day. Many of these patients are elderly and may not have the coordination and dexterity required to manipulate a complex lancet device. Most patients would desire the process for using a lancet device to be as simple, painless, and quick as possible.

Methods for using a traditional lancing devices typically start with a user removing a cap which may cover the lancet's pointed end and manually loading the lancet into lancing device. Next, the lancing device is primed by either pressing a plunger or pulling on a priming mechanism. A trigger is then pulled/pushed to release the stored potential energy and the lancet carriage is propelled forward to pierce the skin of a patient. When the lancing process is complete, the user is required to disassemble the lancing device for safe disposal of the lancet. Unfortunately, this process often includes removing the unprotected lancet while running the risk of unintentional lancing. A special container like a "sharps" container would need to be used for disposal of the unenclosed sharp lancet needle. It would not be unusual for a user to perform an additional step of loading a new lancet in order to save preparation time for the lancet device's next use.

Several improvements have been made to the traditional lancet device. These improvements include:

Lancet cartridges which allow several lancets to be loaded into a single casing at one time (see U.S. Pat. No. 6,472,220).

Complex mechanical means for retracting used lancets back into the casing, such as springs (see U.S. Pat. Nos. 6,071,294 and 6,651,989).

Motorized means for retracting used lancets back into the casing (see US Patent Application Pub. No. 2003/0212424).

Removable and pierceable sterile covers for the lancet needles (see US Patent Application Pub. No. 2003/0153939 and U.S. Pat. No. 5,741,288).

However, these improvements share the major drawback of increasing the part count of a lancing device. Increasing the part count, in turn, increases manufacturing costs, increases the opportunity for defects and malfunctions, and decreases the ease of use of the device. Therefore, there is a need for lancing devices which have a simple design, a low part count, and a low opportunity for defects and malfunctions; while being easy to use and offering improvements such as multiple lancets in one cartridge and a means for safely retracting the lances back into a protective casing after each use.

SUMMARY OF THE INVENTION

In accordance with the current invention, lancet cartridges are provided that have a low part count and a low opportunity for defects and malfunctions. The lancet cartridges of the present invention are suitable used in connection with lancing devices and may be embodied in single-lancet cartridges or in multiple lancets housed within a single cartridge. Further, the lancet cartridges of the invention may retract lancets back into a protective casing after each use.

These and other advantages are obtained through the use of a lancet cartridge that comprises:

(i) a U-shaped support comprising,
   a pair of anchor portions,
   a base portion, and
   a pair of deformable leg portions connecting the anchor portions to the base portion, wherein the pair of deformable leg portions change shape from an initial shape to an extended shape in response to an external applied force and recover to a retracted shape upon removal of the force, and (ii) a lancet,
   the lancet having a tip end, an opposing base end, and an axis extending between the tip end and the base end, wherein a portion of the lancet is disposed between the pair of deformable leg portions of the U-shaped support, wherein:
   the lancet is movable between a starting position, an extended puncturing position, and an ending position along the axis of the lancet in a path defined by the U-shaped support;
   when the lancet is in the starting position, the tip end of the lancet is disposed at least partially through the base portion of the U-shaped support, and the U-shaped support is in the initial shape;
   when the lancet is in the extended puncturing position, the tip end of the lancet is extended through the base of the U-shaped support, and the U-shaped support is in the extended shape; and
   when the U-shaped support recovers to its retracted shape upon removal of the force, the lancet is retracted to the end position by the recovery of the U-shaped support.

In preferred embodiments, the retraction of the deformable leg portions causes the lancet needle to retract out of the patient's skin and return back into the cartridge or the lancing device. In some embodiments of the invention, the lancet cartridge comprises a plurality of U-shaped supports, each with an associated lancet. In the lancet cartridge embodiments of the present invention which comprise a plurality of U-shaped supports, the supports may radially extend from a central axis of the cartridge or may be arranged axially about the central axis. The present invention further provides an improved lancing device comprising the lancet cartridges of the present invention.

BRIEF DESCRIPTION OF THE DRAWINGS

The following is a brief description of the drawings in accordance with the invention.

FIG. 2: The lancet cartridge of FIG. 1 further comprising a housing.

FIG. 5A: A lancing device comprising a lancet cartridge of the present invention where the firing mechanism is in the primed position.

FIG. 5B: A cross-section view of the lancing device of FIG. 5A.

FIG. 5C: A top view of the firing mechanism of the device of FIG. 5A.

FIG. 5D: A cross-section view of the firing mechanism of depicted in FIG. 5C.

FIG. 5E: A side view of the of the firing mechanism of depicted in FIG. 5C.

FIG. 7A: A lancing device comprising a lancet cartridge of the present invention where the firing mechanism is in the neutral position.

FIG. 7B: A cross-section view of the lancing device of FIG. 7A.

FIG. 8: A lancet cartridge in accordance with an embodiment of the present invention.

FIG. 9: A lancet cartridge comprising a sterility plug in accordance with an embodiment of the present invention.

FIG. 10B: A lancing device comprising the lancet cartridge of FIG. 9 wherein the lancet is in the extended puncturing position.

DETAILED DESCRIPTION

Figure 1:
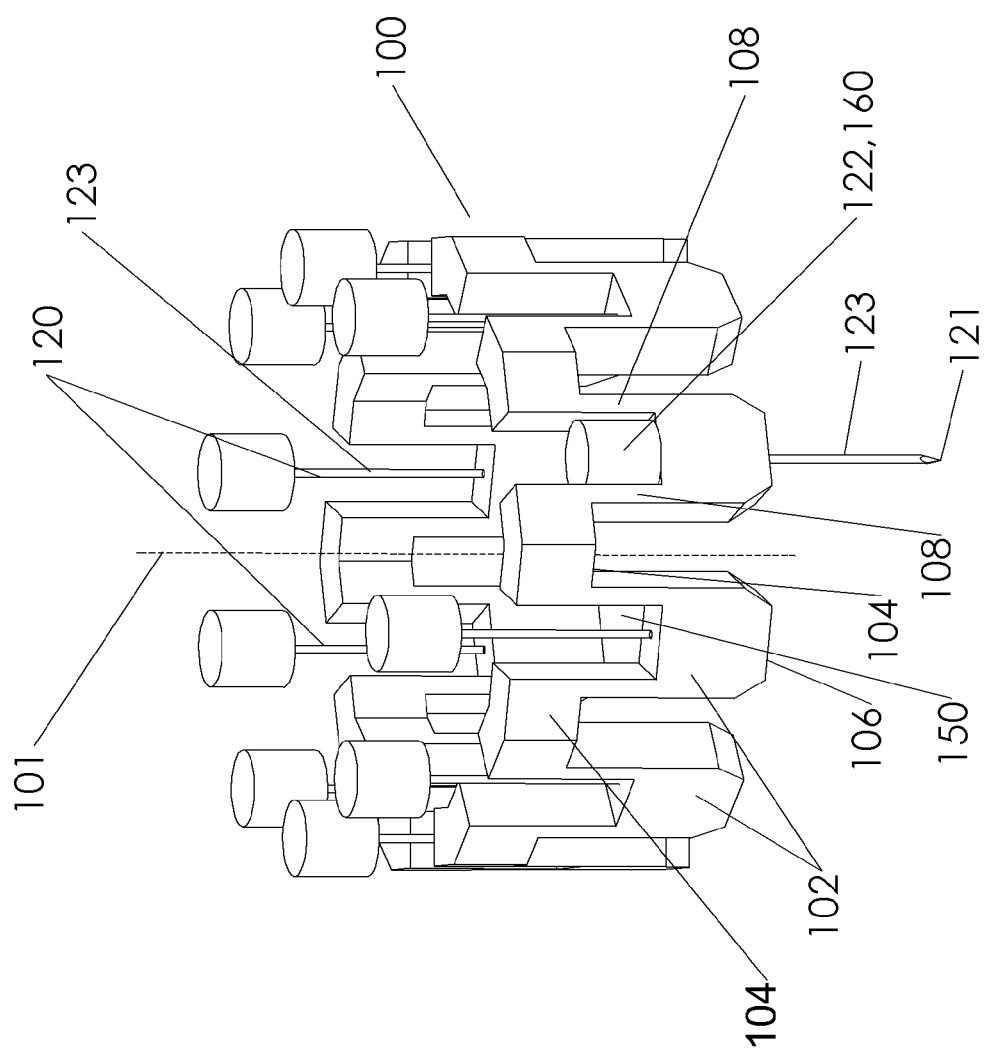
FIG. 1: A lancet cartridge showing multiple lancets and U-shaped supports arranged axially around a circumference about a central axis of the cartridge.

The present invention provides lancet cartridges and improved lancing devices comprising these lancet cartridges. The lancet cartridges and lancing devices of the present invention are user-friendly and easy to use and have low part counts and low opportunity for defects and malfunctions.

Although there are several different methods and apparatuses which may used to practice this invention, the embodiments of the invention share the common element of a U-shaped support having a pair of deformable leg portions and an associated lancet where a portion of the lancet is disposed between the pair of deformable leg portions of the U-shaped support. The deformable leg portions change shape from an initial shape to an extended shape in response to an external applied force that is generally applied via an associated lancing device. The deformable leg portions of the U-shaped support assume a retracted shape which is substantially the same as the initial shape once the force is removed.

Definitions

As used in the specification and claims of this application, the following terms have the following meanings.

Lancet or lancet needle are used interchangeably and refer to a needle or cutting blade used for puncturing/lancing skin. The lancet may be made from a bio-compatible stainless steel or other similar bio-compatible material; each lancet has a tip end, an opposing base end, and a shaft extending along an axis of the lancet between the tip end and the base end. The lancet may be sized to create a wound for bleeding or it may be sized to retrieve a tissue or blood sample (e.g. a biopsy needle).

Lancet cartridge—an apparatus to be used with a lancing device having at least one U-shaped support and at least one lancet associated with the U-shaped support. In specific embodiments, the lancet cartridge comprises a plurality of U-shaped supports each with an associated lancet. Suitable numbers of lancets and U-shaped supports per cartridge are 7, 10, 20, 25, 30 and integral multiples of 7.

Lancing Device—a device used for obtaining biological samples from a patient comprising a space for receiving a lancet cartridge, a hammer, a priming means, a firing mechanism, and a casing, such as the one shown in FIGS. 5A-7E. In preferred embodiments the lancing device is used for acquisition of blood sample from user. In other preferred embodiments the lancing device is used for the acquisition of tissue samples.

U-shaped support—a portion of the lancet cartridge assembly which comprises a pair of anchor portions, a base portion, and a pair of deformable leg portions connecting the anchor portions to the base portion. The pair of deformable leg portions change shape from an initial shape to an extended shape in response to an external applied force and recover to a retracted shape upon removal of the force. The anchor and base portions of the U-shaped support may also be deformable and in one embodiment are made from the same material as the deformable leg portions and formed integral therewith. The deformable leg portions are capable of deforming enough to allow the lancet to extend to its puncturing position, and have sufficient elasticity to provide a restoring force for retracting the lancet to an end position when the external force is removed.

Deformable—in its most basic description: "elastic" or "able to stretch". In more detail the term deformable applies to a property of a material where upon exertion of a force the material extends or stretches from an initial shape to an extended position, then, upon removal of the force the material is retracted to a retracted position that is the same as the initial position or intermediate between the initial position and the extended position. In preferred embodiments, the deformable material retracts substantially back to its initial shape.

Deformable material—materials that are deformable. Suitable materials include without limitation natural elastomers, for example natural rubbers and silicone. Preferably, the deformable material suitable for injection molding to facilitate ease of manufacturing the support.

External Applied Force—a force applied by a hammer under the impetus of a firing mechanism, contained within a lancing device.

Firing mechanism—any of a variety of trigger operated firing mechanisms used for releasing the force required for firing a lancet device, in this case releasing the external force which in turn may cause the U-shaped support to change from its initial shape to its extended shape or drive a lancet towards its puncturing position; an exemplary firing mechanism is illustrated in FIGS. 5A-7E. The external applied force is applied via a hammer or driver that moves toward the lancet in response to the activation of the firing mechanism.

Priming means—any means for storing energy in the lancing device prior to the user initiated activation of the firing mechanism.

Starting Position—the position of the U-shaped support and associated lancet prior to an exertion of an external force causing the U-shaped support to deform and causing the lancet to move in a direction toward its puncturing position.

Extended Puncturing Position—the position of the U-shaped support and lancet after the exertion of an external force has caused the lancet to extend beyond the starting position far enough to enable it to puncture the skin of a patient.

Substantially recovers its initial shape—(with respect to the U-shaped support) means that although the U-shaped support may not completely return to its initial shape, it returns at least enough so that in doing so it causes the lancet to completely retract out of the user's skin and preferably to position wherein the tissue penetrating portion of the lancet is protected by the outer casing of a lancing device.

The Lancing Cartridge

In one embodiment of the present invention the lancet cartridge comprises:
(i) a U-shaped support comprising,
    a pair of anchor portions,
    a base portion, and
    a pair of deformable leg portions connecting the anchor portions to the base portion, wherein the pair of deformable leg portions change shape from an initial shape to an extended shape in response to an external applied force and recover to a retracted shape upon removal of the force, and
(ii) a lancet,
    the lancet having a tip end, an opposing base end, and an axis extending between the tip end and the base end, wherein a portion of the lancet is disposed between the pair of deformable leg portions of the U-shaped support,
wherein:
    the lancet is movable between a starting position, an extended puncturing position, and an ending position along the axis of the lancet in a path defined by the U-shaped support;
    when the lancet is in the starting position, the tip end of the lancet is disposed at least partially through the base portion of the U-shaped support, and the U-shaped support is in the initial shape;
    when the lancet is in the extended puncturing position, the tip end of the lancet is extended through the base of the U-shaped support, and the U-shaped support is in the extended shape; and
    when the U-shaped support recovers to its retracted shape upon removal of the force, the lancet is retracted to the end position by the recovery of the U-shaped support.

In another embodiment the lancet cartridge will further comprise a plurality of U-shaped supports arranged about an axis of the cartridge wherein each of the U-shaped support has an associated lancet. For example, in a preferred embodiment, a lancet cartridge having a cartridge axis comprises:
(i) a plurality of U-shaped supports disposed about the cartridge axis in a generally circular array, each U-shaped support comprising:
    a pair of anchor portions,
    a base portion, and
    a pair of deformable leg portions connecting the anchor portions to the base portion, the pair of deformable leg portions change shape from an initial shape to an extended shape in response to an applied force from the lancet driver and recover to a retracted shape upon removal of the force, and
(ii) a plurality of lancets,
    each lancet associated with a different U-shaped support, and
    each lancet having a tip end, an opposing base end, and an axis extending between the tip end and the base end, wherein a portion of the lancet is disposed between the pair of deformable leg portions of the associated U-shaped support,
wherein:
    each lancet is movable between a starting position, an extended puncturing position, and an ending position along the axis of the lancet in a path defined by the U-shaped support;
    when a selected lancet is in the starting position, the associated U-shaped support is in the initial shape;
    when the selected lancet is in the starting position the tip end of the lancet is disposed at least partially through the base portion of the associated U-shaped support, and the associated U-shaped support is in the initial shape;
    when the selected lancet is in the extended puncturing position, the tip end of the lancet is extended through the base of the associated U-shaped support, and the associated U-shaped support is in the extended shape; and
    when the associated U-shaped support recovers its retracted shape upon removal of the force, the selected lancet is retracted to the end position by the recovery of the U-shaped support.

In one embodiment the lancing cartridge of the present invention comprises a U-shaped support and an associated lancet. The support comprises a pair of anchor portions, a base portion, and a pair of deformable leg portions connecting the anchor portions to the base portion. The pair of deformable leg portions change shape from an initial shape to an extended shape in response to an external applied force and recover to a retracted shape upon removal of the force. The lancet has a tip end, an opposing base end, and a shaft extending along an axis of the lancet between the tip end and the base end. The lancet is movable between a starting position, an extended puncturing position, and an ending position along the axis of the lancet in a path defined by the U-shaped support. When the lancet is in the starting position, the tip end of the lancet is disposed at least partially through the base portion of the U-shaped support, and the U-shaped support is in the initial shape. When the lancet is in the extended puncturing position, the tip end of the lancet is extended through the base of the U-shaped support, and the U-shaped support is in the extended shape. When the U-shaped support recovers to its retracted shape upon removal of the force, the lancet is retracted to the end position.

Figure 3A:
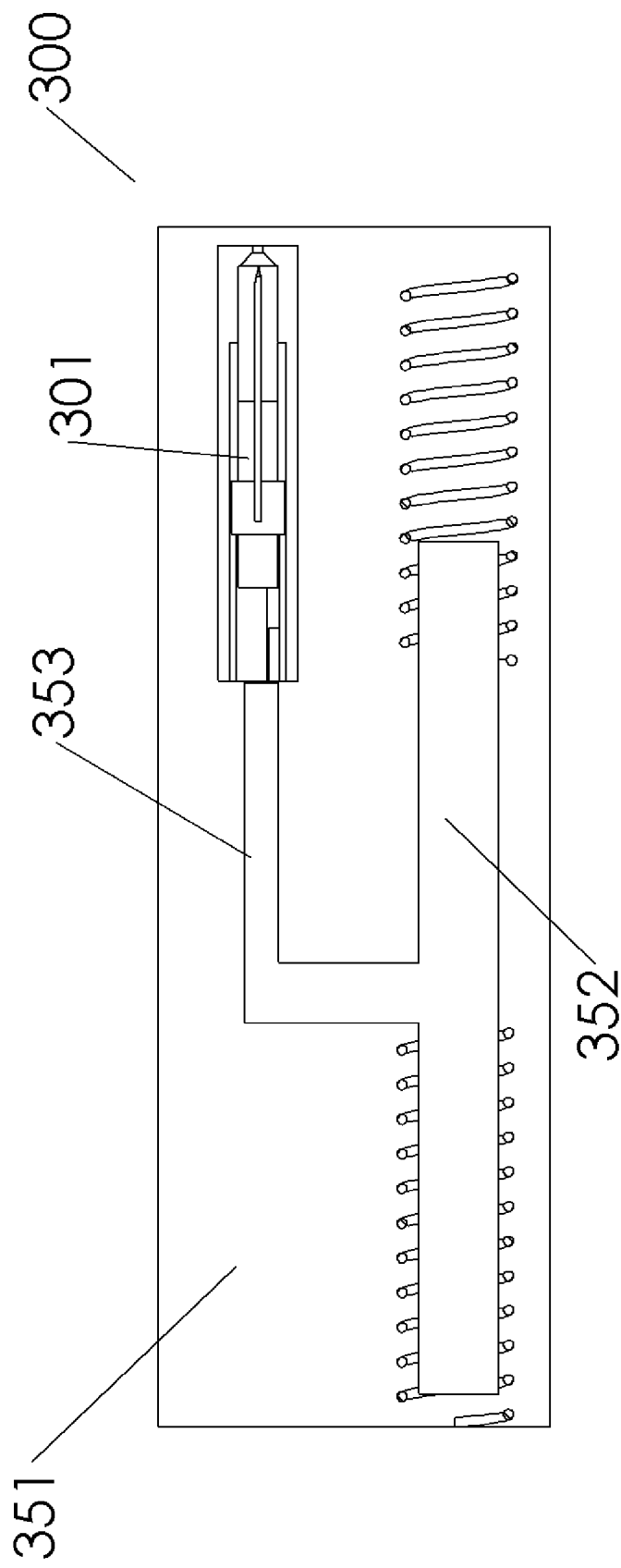
FIG. 3A: A lancing device comprising a lancet cartridge in accordance with an embodiment of the present invention.
Figure 3B:
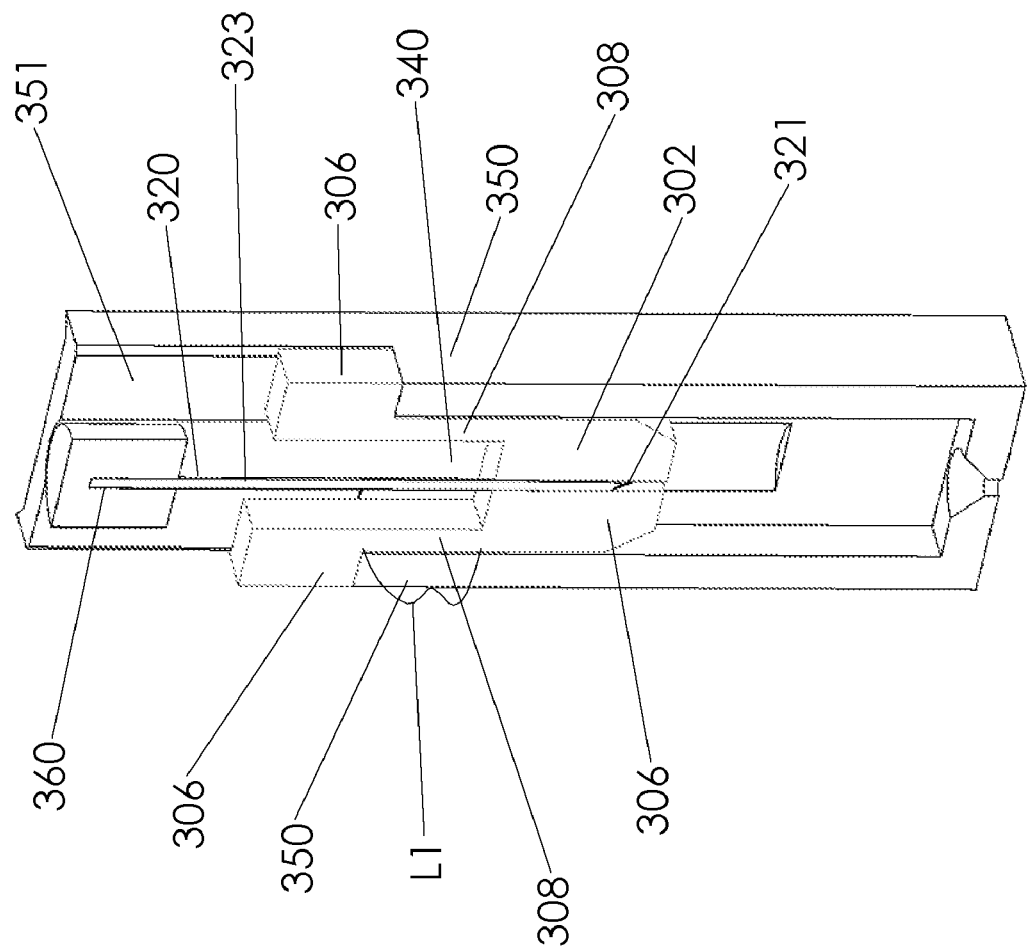
FIG. 3B: A lancet cartridge comprising an individual U-shaped support and associated lancet in a starting position.

FIG. 1 illustrates a preferred embodiment of a lancet cartridge 100 of the present invention wherein the lancet cartridge 100 comprises a plurality of U-shaped supports 102 each with an associated lancet 120. As shown in FIG. 1, each U-shaped support comprises: a pair of anchor portions 104, a base portion 106, and a pair of deformable leg portions 108 connecting the anchor portions 104 to the base portion 106. The pair of deformable leg portions 108 change shape from an initial shape (as shown in FIG. 3A) to an extended shape (as shown in FIG. 3B) in response to an applied force from the hammer of the lancing device and recover to a retracted shape (as show in FIG. 3C) upon removal of the force.

Cartridge 100 further comprises a plurality of lancets 120. Each lancet 120 is associated with a different U-shaped support 102 and each has a tip end 121, an opposing base end 122, and an shaft 123 extending between the tip end 121 and the base end 122 along the axis of the lancet 120. In this and other embodiments of the present invention, at least a portion of each lancet is disposed between the deformable legs 108 of the U-shaped support with the axis of the lancet generally parallel to the direction of deformation of the legs.

In FIG. 1 the base end 122 of lancet 120 has attached to it a driver 160 that interacts with a hammer of an associated lancing device. When a lancet 120 is in the starting position and the associated U-shaped support 102 is in the initial shape, a portion of the lancet 120, here shaft 123, is disposed between the pair of deformable leg portions 108 of the associated U-shaped support 102. In the present embodiment anchor portions 104 interact with the lancing device to provide points where the deformable leg portions 108 extend from and retract to upon lancing operation of the device.

FIG. 2 illustrates another preferred embodiment of the lancet cartridge of the present invention where the plurality of U-shaped supports (not shown) are protected by a cartridge housing 203. The anchor portions of the U-shaped supports in Cartridge 100 interact with housing 203. In the present embodiment the anchor portions of the U-shaped support interact with housing 203 to provide points where the deformable leg portions of the U-shaped support extend from and retract to upon lancing operation of the lancing device.

Figure 3C:
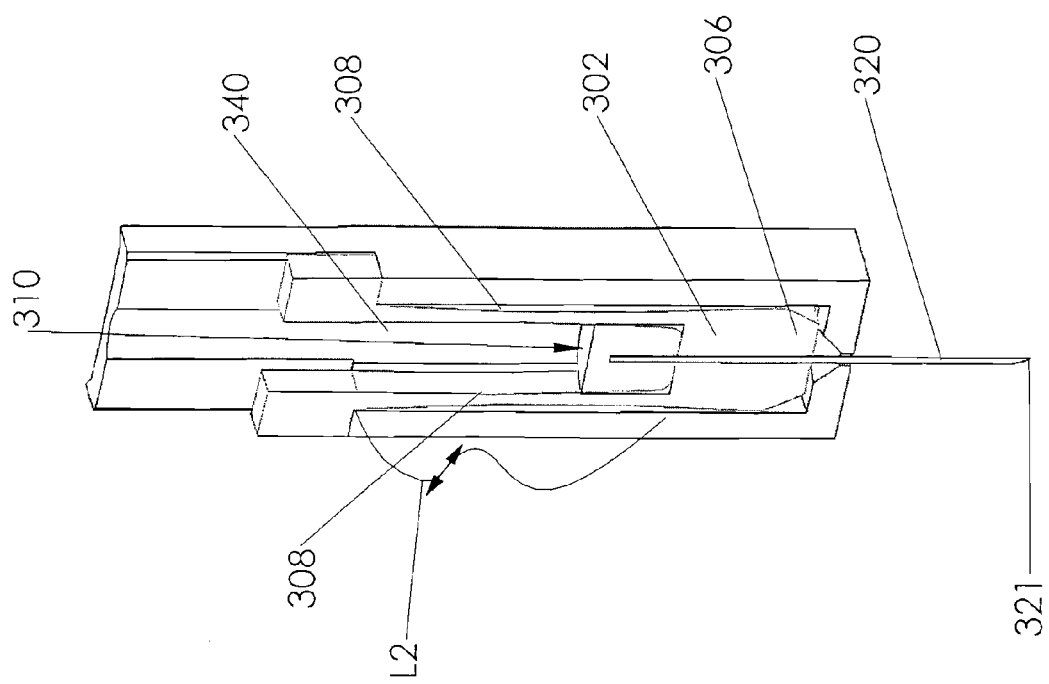
FIG. 3C: A lancet cartridge comprising an individual U-shaped support and associated lancet in an ending position.
Figure 3D:
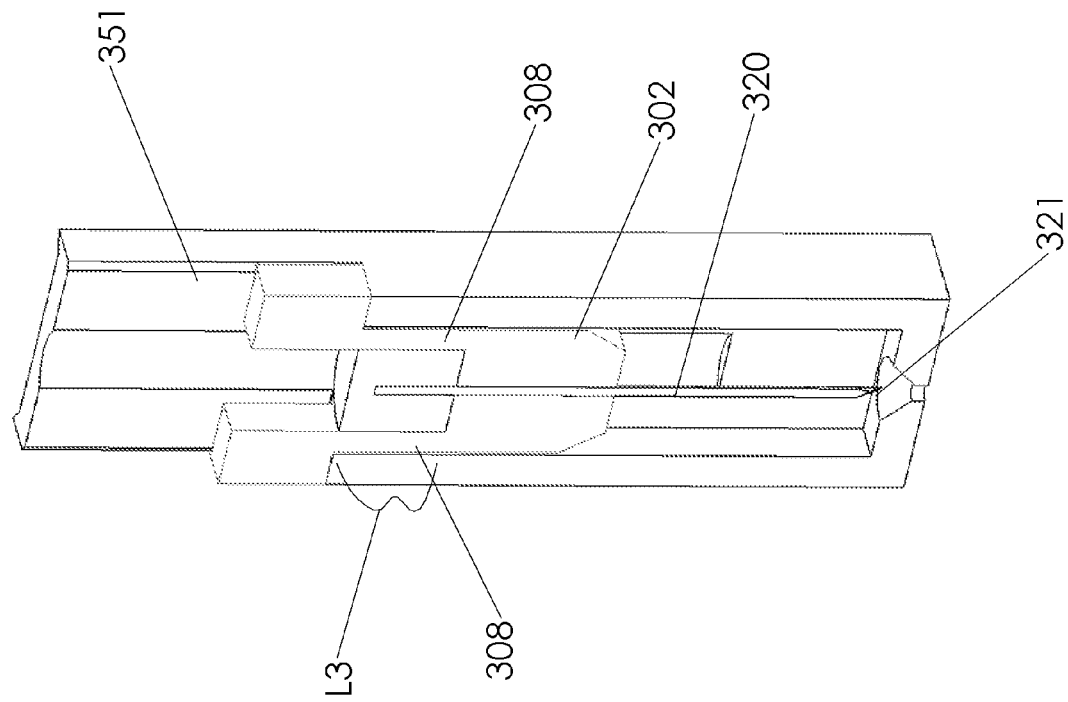
FIG. 3D: A lancet cartridge comprising an individual U-shaped support and associated lancet in a starting position.
Figure 4:
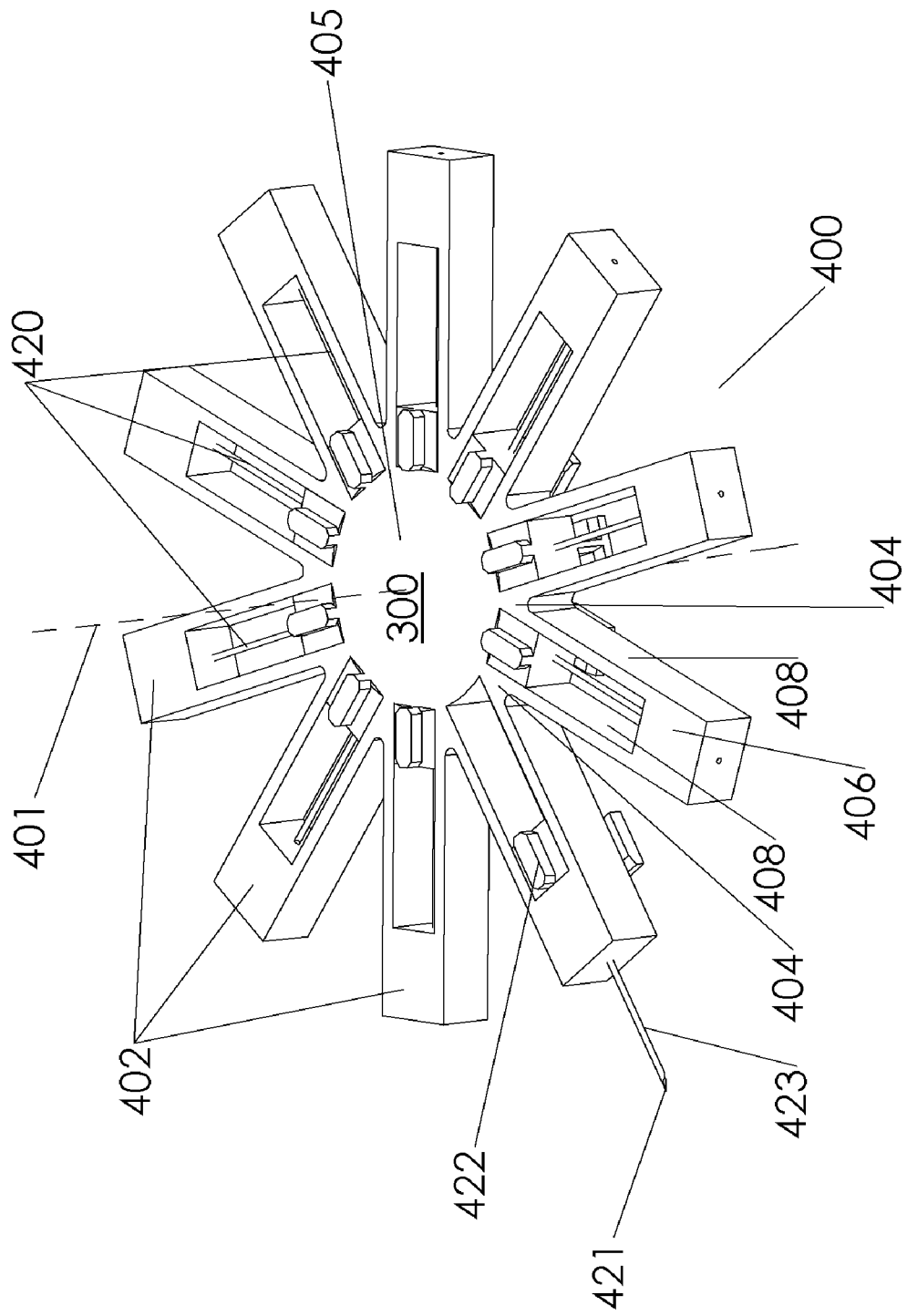
FIG. 4: A lancet cartridge having multiple lancets and U-shaped supports arranged radially about a central axis of the cartridge.
Figure 6B:
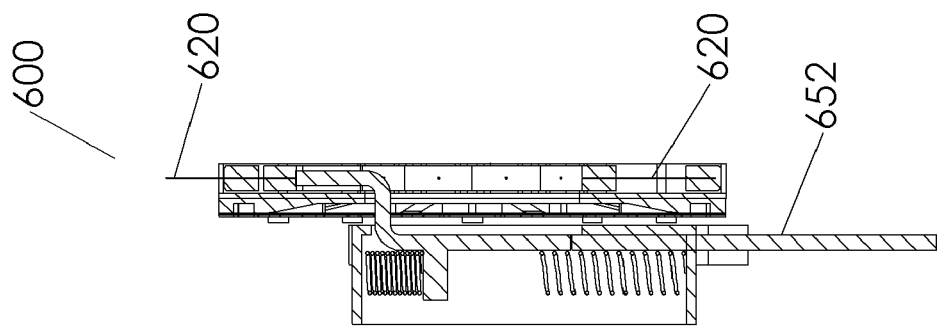
FIG. 6B: A cross-section view of the lancing device of FIG. 6A.
Figure 6A:
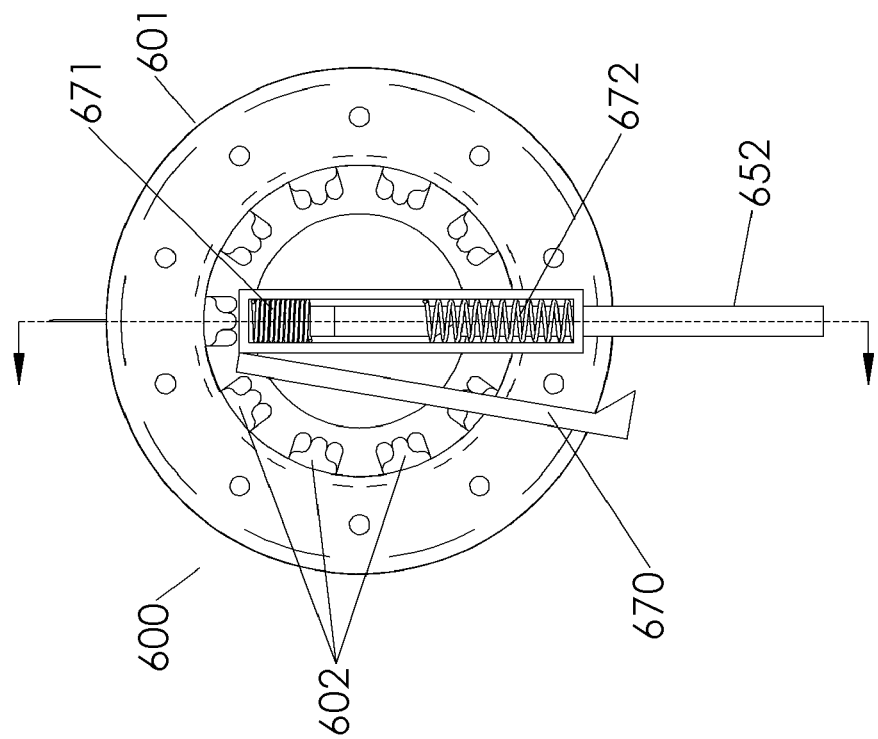
FIG. 6A: A lancing device comprising a lancet cartridge of the present invention where the firing mechanism is in the fired position.
Figure 6E:
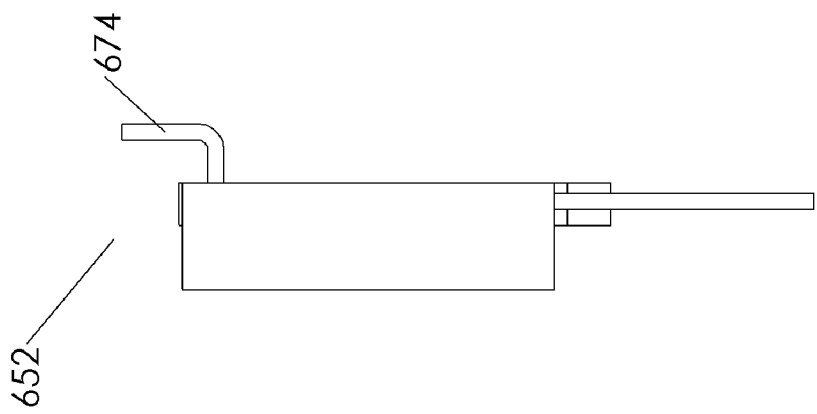
FIG. 6E: A side view of the of the firing mechanism of depicted in FIG. 6C.
Figure 6D:
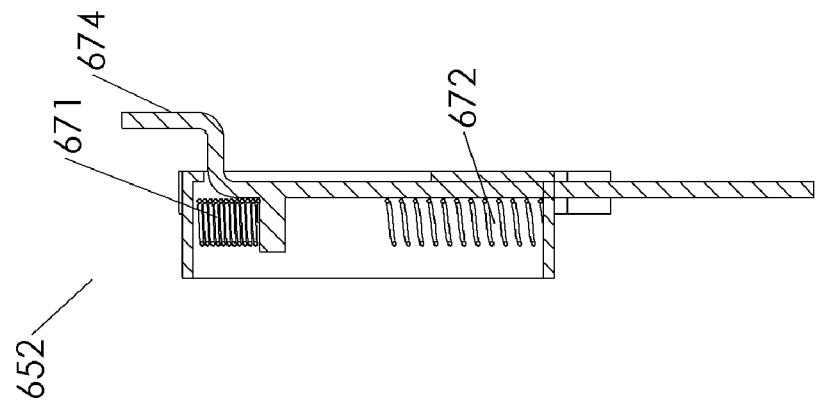
FIG. 6D: A cross-section view of the firing mechanism of depicted in FIG. 6C.
Figure 6C:
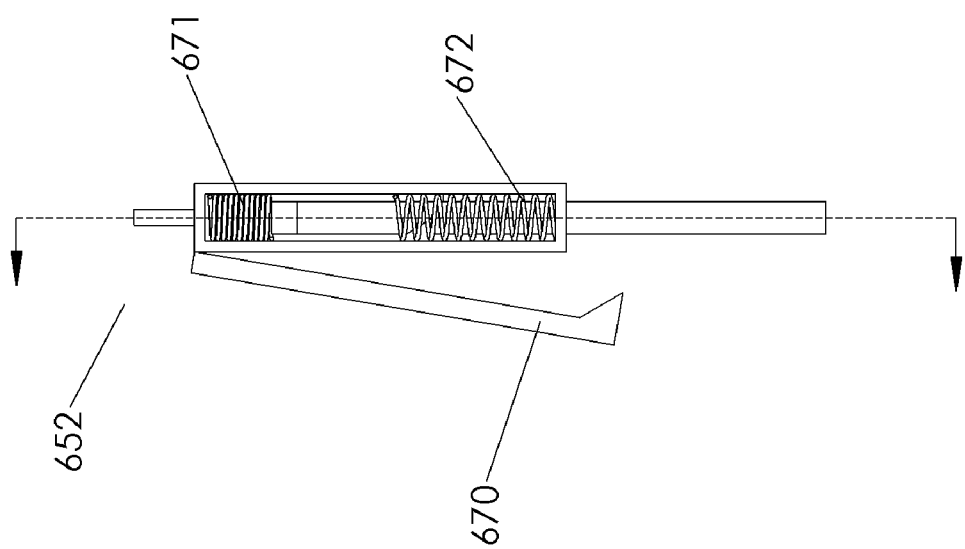
FIG. 6C: A top view of the firing mechanism of the device of FIG. 6A.
Figure 7E:
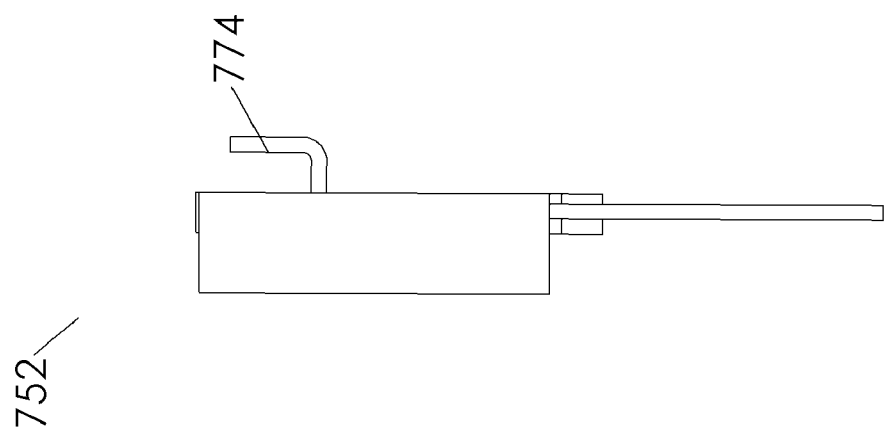
FIG. 7E: A side view of the of the firing mechanism of depicted in FIG. 7C.
Figure 7D:
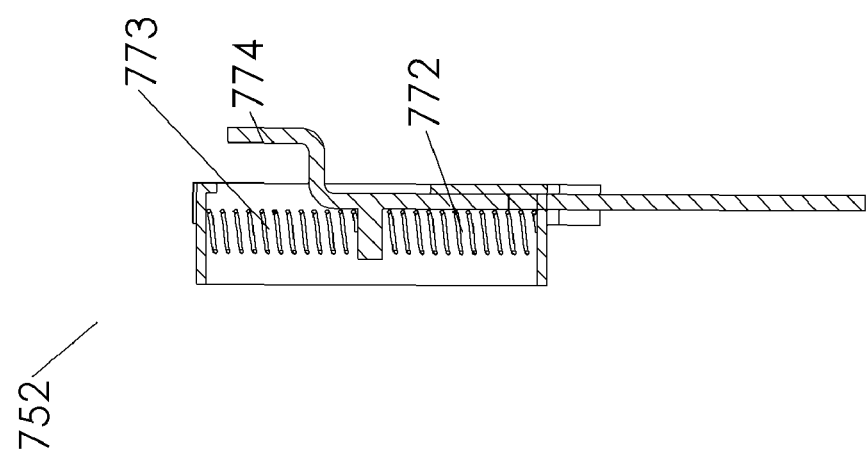
FIG. 7D: A cross-section view of the firing mechanism of depicted in FIG. 7C.
Figure 7C:
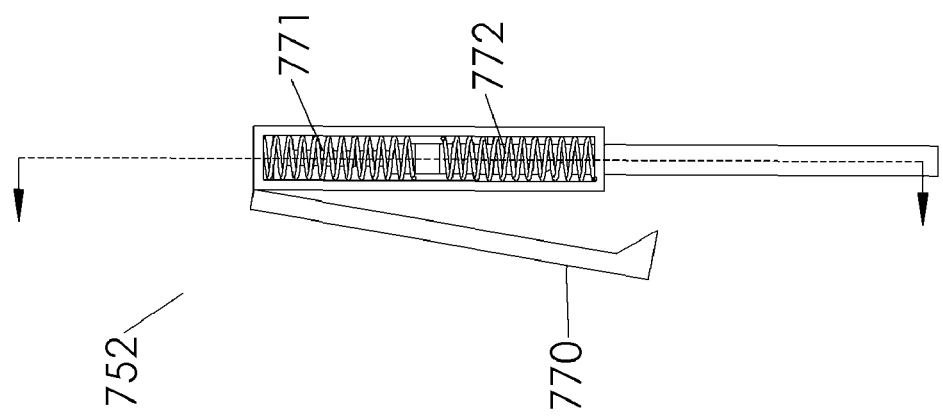
FIG. 7C: A top view of the firing mechanism of the device of FIG. 7A.

In accordance with the embodiments described herein the anchor portions of the U-shaped support provide points where the deformable leg portions extend from and retract to upon lancing operation of the lancing device that comprises the lancet cartridges of the present invention. In certain embodiments the anchor portions directly interact with the either the housing of the cartridge (if present) and/or the lancing device itself, for example with the casing of the lancing device. In preferred embodiments shown in FIGS. 3A-3D, the housing of the lancet cartridge or the casing of the lancing device comprises a series of protrusions 350 formed thereon where upon loading of the lancet cartridge into device or forming of the lancing cartridge comprising the housing shown in FIG. 2, the anchor portions engage the protrusions to provide a point where the anchor portions interact with the cartridge housing (if present) or lancing device to provide points where the deformable leg portions extend from and retract to upon lancing operation of the device. In the embodiment of the lancet cartridge depicted in FIG. 4, the anchor portions 404 of the individual U-shaped supports may or may not directly interact with the cartridge housing (if present) or with a device casing. In FIG. 4, the anchor portions may simply provide points from where the deformable leg portions 408 extend and retract to.

While the lancet cartridges depicted in FIGS. 1 and 2 and other embodiments described herein have a plurality U-shaped supports, it will be appreciated that a lancet cartridge with a single U-shaped support and a single lancet is also within the scope of the invention as is illustrated in FIGS. 3A-3D.

FIG. 3A shows a side view of a lancing device 300 comprising a lancet cartridge 301 in accordance with an embodiment of the present invention. FIGS. 3B-3D show isometric cross-section views of the interaction between protrusions 350 of casing 351 of lancing device 300 and the anchor portions 306 of the U-shaped support 302 as well as the movement of the deformable leg portions 308 of the U-shaped support 302. According to the present embodiment protrusions 350 of casing 351 interact with anchor portions 306 of the lancet cartridge to provide a point where deformable leg portions 308 of the U-shaped support 302 extend from and retract to upon lancing operation of the device 300.

Lancet 320 is movable between a starting position (FIG. 3B), an extended puncturing position (FIG. 3C), and an ending position (FIG. 3D) in a path defined by the U-shaped support. When the lancet 320 is in the starting position (FIG. 3B), the associated U-shaped support 302 is in the initial shape where the deformable leg portions have a length $L_1$ and the tip end 321 of the lancet 320 is disposed partially through the base portion 306 of the associated U-shaped support 302. When the lancet is in the starting position the lancet shaft 323 is disposed between the deformable leg portions 308 of the U-shaped support 302 (i.e. in the U-shaped slot 340 that defines a path of travel of the lancet 320).

When an external force 310 is applied to the lancet 320 it is extended to the puncturing position (FIG. 3C). When the lancet is in the extended puncturing position the tip end 321 of the lancet 320 is extended through the base 306 of the U-shaped support 302, and the associated U-shaped support 302 is in the extended shape (FIG. 3C). When the U-shaped support 302 is in the extended shape the deformable leg portions 308 are stretched to length $L_2$. The external force 310 is applied by hammer 353 of the firing mechanism 352 of the lancing device 300 (FIG. 3A).

Upon removal of force 310, the U-shaped support 302 substantially recovers to its retracted shape (FIG. 3C) and the lancet 320 is retracted to the end position as the deformable leg portions 308 retract to a length $L_3$. As described herein, in preferred embodiments length $L_3$ is the substantially the same as length $L_1$. In the present embodiment, when the lancet 320 is retracted to the end position its tip end 321 is protected by the casing 351.

The U-shaped slot 340 has a proximal end toward the anchor portion of the U-shaped support and a distal end toward the base end 306 of the U-shaped support 302. The starting position of the base end of the lancet with driver head 360 is at the proximal end of the U-shaped slot 340 toward the anchor portions 306. When force 310 is applied to the lancet through driver 360 (FIG. 3C) the base end of lancet 320 and driver 360 are driven from the proximal end of the U-shaped slot 340 to the distal end of the U-shaped slot 340 toward the base 306 of the U-shaped support 302. Upon or during driving the base end of the lancet 320 toward the distal end of the U-shaped slot 340, the lancet 320 pierces the base end 306 of the U-shaped support 302. Upon removal of the external force 310, the U-shaped support 302 substantially recovers its initial shape causing by the retraction of deformable leg portions 308 thereby retracting the lancet 320 to its end position (FIG. 3D).

The embodiments of the present invention described above with reference to FIGS. 3A-3D illustrate a lancet cartridge comprising a single U-shaped support with a single lancet associated therewith. In the embodiments of the present invention where the lancet cartridges comprise a plurality of U-shaped supports and a plurality of lancets, the movement of an individual U-shaped support and its associated lancet can be also described using the description of FIGS. 3A to 3D.

As depicted in the embodiments shown in FIGS. 1 and 2 the plurality of U-shaped supports are disposed about a central axis 101, 201 of the cartridge 100, 200 in a generally circular array. In these embodiment the deformable leg portions of each of the U-shaped supports and the axises of the associated lancets are arranged about and parallel to the cartridge axis 101, 201 of the cartridge 100, 200.

FIG. 4 illustrates an embodiment of the invention which comprises a lancet cartridge 400 having a plurality of U-shaped supports 402 and a plurality of lancets 420 disposed in a generally circular array about cartridge axis 401. In FIG. 4, they extend radially from the cartridge axis 401. Each U-shaped support comprises a pair of anchor portions 404, a base portion 406, and a pair of deformable leg portions 408 connecting the anchor portions 404 to the base portion 406, the pair of deformable leg portions 408 change shape from an initial shape to an extended shape in response to an applied force from the lancet driver and recover to a retracted shape upon removal of the force.

The deformable leg portions 408 extend radially from a center portion 405 that may be solid or hollow and may or may not be made from of the same material as the U-shaped supports. Each lancet 420 has a tip end 421, an opposing base end 422, and an shaft 423 extending between the tip end 421 and the base end 422. The lancet 420 is movable between a starting position, an extended puncturing position, and an ending position along the axis of the lancet in a path defined by the support.

The material of the deformable leg portions of the U-shaped support controls how well the support is able to recover back to its original shape after being stretched during lancing operation of the lancing device. The ideal amount of recovery is for the support to recover enough of its shape to retract the lancet tip back into the casing of the lancing device, however, some U-shaped supports may retract only enough to cause the needle to retract from the tissue it punctures. It will be appreciated that for deformation of the deformable leg portions of the U-shaped support to occur, there must be resistance to movement of the support in response to the applied force. This is suitably provided by an interaction of the deformable leg portions with the anchor portions of the U-shaped support. In one embodiment the anchor portions interact with housing of the lancet cartridge (if present as described above) or with the casing of the lancing device to provide points from where the deformable leg portions extend from and return toward.

In the lancet cartridges of the invention the tip end of the lancet is at least partially through the base portion. This means that the tip end is embedded within the base portion or has passed through the base portion and is on a side of the base portion opposite the base end of the lancet. By way of example, the embodiments described with reference to FIGS. 1, 2, 3A-3D, and 4 when the lancet is in the initial position, the tip end 121, 321, 421 of the lancet 120, 320, 420 is disposed partially through the base 106, 306, 406 of the U-shaped support 102, 302, 402 which serves both to maintain sterility of the lancet prior to use and to protects the user from accidental pricking when loading such into the lancing device. In preferred embodiments, the lancet is retracted to a position that is also within the support after use. FIG. 8 shows an embodiment in which the tip end 821 of lancet 820 is disposed entirely through base 806 of U-shaped support 802.

Figure 10A:
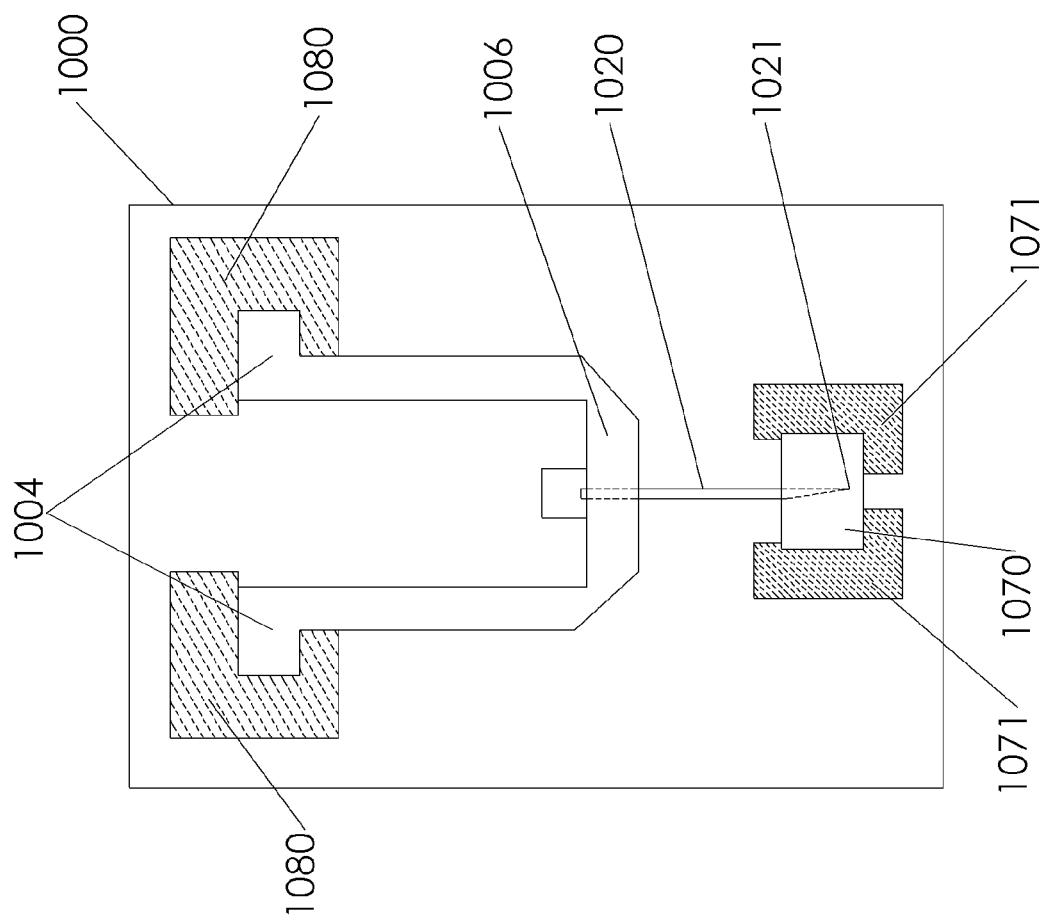
FIG. 10A: A lancing device comprising the lancet cartridge of FIG. 9 wherein the lancet is in the initial or neutral position.

In embodiments where the tip end of the lancet is disposed at a position that is entirely through the base end of the U-shaped support when the lancet is in its starting position and the U-shaped support is in its initial position, for example as depicted in FIG. 8, the tip end 921 of the lancet 920 is preferably covered by a sterility plug 970 (as shown in FIG. 9) to maintain sterility of the lancet 920 prior to use and to protect the user according to above. The user may remove the sterility plug prior to using an associated lancing device. However, in a preferred embodiment a preferred lancing device for use with a lancet cartridge in accordance with the present embodiment and as that shown in FIGS. 10A and 10B, will comprise a sterility plug receiving protrusion(s) 1071. In the lancing device 1000 embodiments of FIGS. 10A and 10B the sterility plug 1070 is made from a pierceable material, such as that of the base of the U-shaped support which is received in the receiving protrusions 1071 of the lancing device. FIG. 10A shows the lancet in its starting position and the U-shaped support in its initial position. Tip end 1021 of lancet 1020 is disposed entirely through base end 1006 of the U-shaped support and into sterility plug 1070. As force 1010 is applied to the base end of lancet 1020, the deformable leg portions 1008 of the U-shaped support 1002 elongate and the tip end 1021 of lancet 1020 is pushed through the sterility plug 1070, out of the casing 1051 of the lancing device 1000 and into the skin 1099 of a user. Upon removal of force 1010 the deformable leg portions 1008 of the U-shaped support retract thereby retrieving the tip end 1021 of the lancet 1020 from the user's skin 1099 back into sterility plug 1070 preferably as depicted in FIG. 10A. In preferred embodiments the tip end 1021 of lancet 1020 will be retracted to a position entirely within the sterility plug so as to prevent the tip end from being exposed after it has been used thereby protecting the user of the device from accidently pricking themselves with the same upon removal of the cartridge from the device.

The Lancing Device and the Firing Mechanism:

The lancet cartridges of the present invention as described above may be directly loaded into a lancing device adapted to receive the same. In one embodiment as shown in FIGS. 10A and 10B, the anchor portions 1004 of the U-shaped support(s) 1002 interact with corresponding anchor protrusions 1080 of the device housing thereby creating anchor point for the U-shaped support where the deformable leg portions may extend from and return to during lancing operation of the device. In another embodiment of the present invention shown in FIG. 2 a plurality of U-shaped supports are protected by a cartridge housing 203 where the anchor portions of the U-shaped supports interact with corresponding anchor protrusions formed on inside of housing 203. The cartridge with housing shown in FIG. 2 may be directly loaded into lancing device.

In use, an external force is applied to either the support or the lancet which causes the deformable leg portions of the U-shaped support to change shape. The source of this external force is a typical firing mechanism which is commonly found in many lancet devices. An illustration of a preferred lancing device 500, in its primed position, comprising a lancet cartridge 501 having a plurality of U-shaped supports 502 and associated lancets 520 is depicted in FIG. 5A with a cross-sectional side view of the same shown in FIG. 5B. The firing mechanism 552 of the present embodiment is in its primed position as shown in FIG. 5C with a cross-sectional side view of the same depicted in FIG. 5D and a plane side view depicted in FIG. 5E. The firing mechanism 552 includes the following components: a firing latch 570, a return spring 571, a firing spring 572, a case/body 573, and a hammer 574. The hammer 574 of the firing mechanism is typically designed to work with any of the embodiments of the lancet cartridges described herein. The same lancing device is depicted in the same views when it is in the fired position 600 in FIGS. 6A-6E, and in the neutral position 700 in FIGS. 7A-7E.

The firing mechanism 552, 652, 752 works by compression of the firing spring 572, 672, 772 (shown in FIGS. 5A to 5E) and release of energy in the firing spring 572, 672, 772 (shown in FIGS. 6A-6E). The firing spring 572, 672, 772 compression (shown in FIGS. 5A to 5E) stores potential energy which is release upon the unlatching of the firing latch 570, 670, 770 (shown in FIGS. 6A-6E). The unlatching of the firing latch 570, 670, 770 causes the energy stored in firing spring 572, 672, 772 to be released thereby driving the hammer 574, 674, 774 from a primed position (shown in FIGS. 5A-5E) to a lanced position (shown in FIGS. 6A-6E). The hammer 574, 674, 774 makes contact with a lancet of the lancet cartridges of the invention (thereby applying the "external force" or the lancing force). After the release of the stored energy in firing spring 572, 672, 772 the return spring 571, 671, 771 engages and returns the hammer 574, 674, 774 toward a neutral position shown in FIGS. 7A-7E. In one embodiment the deformable leg portions of the U-Shaped support would act in place of or in combination with return spring 571, 671, 771 to return the hammer shown 574, 674, 774 to its resting position as the deformable leg portions retract toward their initial shape.

The lancet cartridges of the present invention may be used with lancing devices described above that are adapted to receive the lancet cartridges of the present invention. Thus in another embodiment the present invention provides a lancing device comprising a lancet cartridge and a firing mechanism having a firing hammer, wherein the lancet cartridge comprises:
(i) a U-shaped support comprising,
   a pair of anchor portions,
   a base portion, and
   a pair of deformable leg portions connecting the anchor portions to the base portion, wherein the pair of deformable leg portions change shape from an initial shape to an extended shape in response to an external applied force and recover to a retracted shape upon removal of the force, and
(ii) a lancet,
   the lancet having a tip end, an opposing base end, and an axis extending between the tip end and the base end, wherein a portion of the lancet is disposed between the pair of deformable leg portions of the U-shaped support,
wherein:
   the firing hammer engages the lancet cartridge and drives a selected lancet from a starting position to an extended puncturing position,
   the lancet is movable between a starting position, an extended puncturing position, and an ending position along the axis of the lancet in a path defined by the U-shaped support;
   when the lancet is in the starting position, the tip end of the lancet is disposed at least partially through the base portion of the U-shaped support, and the U-shaped support is in the initial shape;
   when the lancet is in the extended puncturing position, the tip end of the lancet is extended through the base of the U-shaped support, and the U-shaped support is in the extended shape; and
   when the U-shaped support recovers to its retracted shape upon removal of the force, the lancet is retracted to the end position by the recovery of the U-shaped support.

It should be appreciated that even though only one exemplary embodiment of a firing mechanism was shown which would work with the lancet cartridges of the invention, that other similar and common firing mechanisms well know in the lancet industry would be able to be used as well.

Various firing spring types may be used. The firing springs may be elongated, deflected or radially round to store potential energy for future release.

The invention claimed is:

1. A lancet cartridge comprising:
(i) a U-shaped support comprising,
   a pair of anchor portions,
   a base portion, and
   a pair of deformable leg portions connecting the anchor portions to the base portion, wherein the pair of deformable leg portions change shape from an initial shape to an extended shape in response to an external applied force and recover to a retracted shape upon removal of the force, wherein the deformable leg portions extend from and retract toward their respective anchor portion, and
(ii) a lancet,
   the lancet having a tip end, an opposing base end, and an axis extending between the tip end and the base end, wherein a portion of the lancet is disposed between the pair of deformable leg portions of the U-shaped support,
wherein:
   the lancet is movable between a starting position, an extended puncturing position, and an ending position along the axis of the lancet in a path defined by the U-shaped support;
   when the lancet is in the starting position, the tip end of the lancet is disposed at least partially through the base portion of the U-shaped support, and the U-shaped support is in the initial shape;
   when the lancet is in the extended puncturing position, the tip end of the lancet is extended through the base of the U-shaped support, and the U-shaped support is in the extended shape; and
   when the U-shaped support recovers to its retracted shape upon removal of the force, the lancet is retracted to the end position by the recovery of the U-shaped support.

2. The lancet cartridge of claim 1 further comprising:
a cartridge axis;
a plurality of U-shaped supports disposed about the cartridge axis in a generally circular array; and
a plurality of lancets, wherein each lancet is associated with an individual U-shaped support.

3. The lancet cartridge of claim 2, wherein the deformable leg portions of each of the U-shaped supports and the axes of the associated lancets extend radially from the cartridge axis.

4. The lancet cartridge of claim 2, wherein the deformable leg portions of each of the U-shaped supports and the axes of the associated lancets are arranged about and parallel to the cartridge axis.

5. The lancet cartridge of claim 2, further comprising a housing comprising a plurality of anchor protrusions that engage the anchor portions of each of the U-shaped supports to provide anchor points for the extension and retraction of the deformable leg portions of the U-shaped supports.

6. The lancet cartridge of claim 1, further comprising a sterility plug, wherein the tip end of the lancet is disposed through the base portion of the U-shaped support and into the sterility plug when the lancet is in the starting position.

7. The lancet cartridge of claim 6, wherein the tip end of the lancet is disposed through the base portion of the U-shaped support and into the sterility plug when the lancet is in the end position.

8. The lancet cartridge of claim 6, further comprising a housing comprising a pair of anchor protrusions that engage the anchor portions of the U-shaped support to provide anchor points for the extension and retraction of the deformable leg portions of the U-shaped support.

9. A lancet cartridge having a cartridge axis, the cartridge comprising:
(i) a plurality of U-shaped supports disposed about the cartridge axis in a generally circular array, each U-shaped support comprising:
a pair of anchor portions,
a base portion, and
a pair of deformable leg portions connecting the anchor portions to the base portion, the pair of deformable leg portions change shape from an initial shape to an extended shape in response to an applied force from a lancet driver and recover to a retracted shape upon removal of the force, wherein the deformable leg portions extend from and retract toward their respective anchor portion, and
(ii) a plurality of lancets,
each lancet associated with a different U-shaped support, and
each lancet having a tip end, an opposing base end, and an axis extending between the tip end and the base end, wherein a portion of the lancet is disposed between the pair of deformable leg portions of the associated U-shaped support,
wherein:
each lancet is movable between a starting position, an extended puncturing position, and an ending position along the axis of the lancet in a path defined by the U-shaped support;
when a selected lancet is in the starting position, the associated U-shaped support is in the initial shape;
when the selected lancet is in the starting position the tip end of the lancet is disposed at least partially through the base portion of the associated U-shaped support, and the associated U-shaped support is in the initial shape;
when the selected lancet is in the extended puncturing position, the tip end of the lancet is extended through the base of the associated U-shaped support, and the associated U-shaped support is in the extended shape; and
when the associated U-shaped support recovers to its retracted shape upon removal of the force, the selected lancet is retracted to the end position by the recovery of the U-shaped support.

10. The lancet cartridge of claim 9, wherein the deformable leg portions of each of the U-shaped supports and the axes of the associated lancets extend radially from the cartridge axis.

11. The lancet cartridge of claim 9, wherein the deformable leg portions of each of the U-shaped supports and the axes of the associated lancets are arranged about and parallel to the cartridge axis.

12. The lancet cartridge of claim 9, further comprising a plurality of sterility plugs, wherein the tip end of each of the lancets is disposed through the base portion of its associated U-shaped support and into one of the plurality of sterility plugs when the lancet is in the starting position.

13. The lancet cartridge of claim 12, wherein the tip end of the lancet is disposed through the base portion of the U-shaped support and into the associated sterility plug when the lancet is in the end position.

14. The lancet cartridge of claim 9, further comprising a housing comprising a plurality of anchor protrusions that engage the anchor portions of each of the U-shaped supports to provide anchor points for the extension and retraction of the deformable leg portions of the U-shaped supports.

15. A lancing device comprising a lancet cartridge and a firing mechanism having a firing hammer, wherein the lancet cartridge comprises:
(i) a U-shaped support comprising,
a pair of anchor portions,
a base portion, and
a pair of deformable leg portions connecting the anchor portions to the base portion, wherein the pair of deformable leg portions change shape from an initial shape to an extended shape in response to an external applied force and recover to a retracted shape upon removal of the force, wherein the deformable leg portions extend from and retract toward their respective anchor portion, and
(ii) a lancet,
the lancet having a tip end, an opposing base end, and an axis extending between the tip end and the base end, wherein a portion of the lancet is disposed between the pair of deformable leg portions of the U-shaped support,
wherein:
the firing hammer engages the lancet cartridge and drives a selected lancet from a starting position to an extended puncturing position,
the lancet is movable between a starting position, an extended puncturing position, and an ending position along the axis of the lancet in a path defined by the U-shaped support;
when the lancet is in the starting position, the tip end of the lancet is disposed at least partially through the base portion of the U-shaped support, and the U-shaped support is in the initial shape;
when the lancet is in the extended puncturing position, the tip end of the lancet is extended through the base of the U-shaped support, and the U-shaped support is in the extended shape; and
when the U-shaped support recovers to its retracted shape upon removal of the force, the lancet is retracted to the end position by the recovery of the U-shaped support.

16. The lancing device of claim 15 wherein the lancet cartridge further comprises:
a cartridge axis;
a plurality of U-shaped supports disposed about the cartridge axis in a generally circular array; and
a plurality of lancets, wherein each lancet is associated with an individual U-shaped support.

17. The lancing device of claim 16, wherein the deformable leg portions of each of the U-shaped supports and the axes of the associated lancets extend radially from the cartridge axis.

18. The lancing device of claim 16, wherein the deformable leg portions of each of the U-shaped supports and the axes of the associated lancets are arranged about and parallel to the cartridge axis.

19. The lancing device of claim 15, wherein the lancet cartridge further comprises a sterility plug, wherein the tip end of the lancet is disposed through the base portion of the U-shaped support and into the sterility plug when the lancet is in the starting position.

20. The lacing device of claim 19, wherein the tip end of the lancet is disposed through the base portion of the U-shaped support and into the sterility plug when the lancet is in the end position.

* * * * *